United States Patent
Burnside et al.

(10) Patent No.: US 6,890,918 B2
(45) Date of Patent: May 10, 2005

(54) PHARMACEUTICAL COMPOSITIONS INCLUDING ACE/NEP INHIBITORS AND BIOAVAILABILITY ENHANCERS

(75) Inventors: Beth Burnside, Bethesda, MD (US); Rong-Kun Chang, Rockville, MD (US); Amir Shojaei, Gaithersburg, MD (US)

(73) Assignee: Shire Laboratories, Inc., Rockville, MD (US)

( * ) Notice: Subject to any disclaimer, the term of this patent is extended or adjusted under 35 U.S.C. 154(b) by 355 days.

(21) Appl. No.: 10/134,651

(22) Filed: Apr. 30, 2002

(65) Prior Publication Data

US 2003/0096761 A1 May 22, 2003

Related U.S. Application Data (60) Provisional application No. 60/287,535, filed on Apr. 30, 2001.

(51) Int. Cl.⁷ ...................... A61K 31/554; A61K 31/36; A61K 31/195
(52) U.S. Cl. ................... 514/211.05; 514/466; 514/562
(58) Field of Search ................................. 514/474, 562, 514/574, 211.05, 466

(56) References Cited

U.S. PATENT DOCUMENTS 4,454,125 A * 6/1984 Demopoulos ................ 514/52
4,975,444 A 12/1990 Danilewicz et al.
5,897,876 A 4/1999 Rudnic et al.

FOREIGN PATENT DOCUMENTS

WO    WO 99/65500    12/1999

OTHER PUBLICATIONS

Structure of Sampatrilat, Merck Index Abstract # 8428 (2004).*
EP International Search Report dated Sep. 4, 2002 of PCT/US02/13301.
EP International Search Report dated Sep. 4, 2002.

* cited by examiner

Primary Examiner—Raymond J. Henley, III
(74) Attorney, Agent, or Firm—M. Elisa Lane (57) ABSTRACT

A pharmaceutical composition comprising an inhibitor of angiotensin converting enzyme and neutral endopeptidase, such as sampatrilat, and at least one bioavailability enhancer such as an organic acid, e.g., ascorbic acid. Such a composition has improved systemic bioavailability.

18 Claims, 6 Drawing Sheets

Figure 5. Transport Enhancement of Sampatrilat Across Caco-2 Cell Model

Figure 6. Mean Plasma Concentration Versus Time Curves for Sampatrilat Formulations

PHARMACEUTICAL COMPOSITIONS INCLUDING ACE/NEP INHIBITORS AND BIOAVAILABILITY ENHANCERS

This application claims the benefit of U.S. Provisional Application U.S. 60/287,535, filed Apr. 30, 2001, the entirety of which is hereby incorporated by reference.

FIELD OF THE INVENTION

This invention relates to pharmaceutical compositions containing inhibitors of angiotensin converting enzyme (ACE) and/or neutral endopeptidase (NEP), which have improved systemic bioavailability. More particularly, this invention relates to pharmaceutical compositions containing an ACE and/or NEP inhibitor in combination with a bioavailability enhancer.

BACKGROUND OF THE INVENTION

Sampatrilat is a dual inhibitor of angiotensin converting enzyme (ACE) and neutral endopeptidase (NEP), with potential application as an antihypertensive agent as well as an agent for treatment of congestive heart failure. Because of this unique dual modality, sampatrilat does not cause a sudden and significant drop in blood pressure after administration of the first dose. In addition, sampatrilat and has a much lower propensity to cause common side effects such as dry cough. However, the oral bioavailability of sampatrilat has been reported to be low, as low as 5% in dogs and 2% in man. Clinical pharmacokinetic data show generally low but persistent plasma drug exposure following single and multiple doses.

Consequently, there is a need to provide pharmaceutical formulations which comprise sampatrilat or similar agents that exhibit enhanced oral absorption of the drug and thereby improve its therapeutic efficacy is timely.

SUMMARY OF THE INVENTION

In accordance with an aspect of the present invention, there is provided a pharmaceutical composition comprising at least one inhibitor of angiotenisin converting enzyme and/or neutral endopeptidase and at least one bioavailabilty enhancer in an amount effective to enhance the oral bioabsorption of said at least one inhibitor.

In accordance with an aspect of the present invention, there is provided a pharmaceutical composition comprising at least one inhibitor of angiotenisin converting enzyme and/or neutral endopeptidase and an effective amount of at least one bioavailabilty enhancer, wherein bioavailabilty enhancer is an organic acid.

In accordance with the present invention there is also provided a method for the treatment or prevention of cardiovascular disorders including hypertension and heart failure comprising administering a pharmaceutically effective amount of a formulation of the present invention to a subject in need of such treatment or prevention.

In accordance with the present invention there is further provided the use of a pharmaceutically effective amount of a formulation of the present invention for treating or preventing cardiovascular disorders including hypertension and heart failure.

In accordance with the present invention there is also provided a method for the manufacture of a pharmaceutical formulation comprising combining at least one pharmaceutical agent, in powder form, wherein said agent is an inhibitor of angiotensin converting enzyme and/or an inhibitor of neutral endopeptidase, with an organic acid in powder form to obtain a powdered mixture, and either (a) encapsulating the powdered mixture in a capsule or (b) forming said powdered mixture into a tablet.

BRIEF DESCRIPTION OF THE DRAWINGS

Various features and attendant advantages of the present invention will be more fully appreciated as the same becomes better understood when considered in conjunction with the accompanying drawings wherein.

DETAILED DESCRIPTION OF THE INVENTION

The pharmaceutical compositions/formulations in accordance with the invention exhibit enhanced bioavailability of an ACE inhibitor, an NEP inhibitor, or, like in the case of sampatrilat, an agent which inhibits both ACE and NEP. Such dual inhibitors are preferred.

Suitable inhibitors of angiotensin converting enzyme and/or neutral endopeptidase which may be included in the composition include, but are not limited to, sampatrilat, fasidotril, omapatrilat, enalaprilat, and mixtures thereof. In accordance with a further embodiment of the invention, the inhibitor of angiotensin converting enzyme and/or neutral endopeptidase is sampatrilat.

In accordance with one embodiment, the bioavailability enhancers used in accordance with the invention are organic acids, pharmaceutically acceptable salts of organic acids, sodium lauryl sulfate, palmitoyl carntine, or mixtures thereof. The formulations of these bioavailability enhancers and the ACE/NEP inhibitors can be used in powdered form, for example, as tablets or powder filled capsules, or in liquid form, e.g., capsules filled with liquid dispersions.

Thus, the pharmaceutical compositions can be formulated in various solid dosage forms for orally administering the agents and bioavailability enhancers including such solid forms as tablets, gelcaps, capsules, caplets, granules, lozenges and bulk powders. The formulations can contain various other conventional pharmaceutical excipients such as various pharmaceutically acceptable carriers, diluents (such as sucrose, mannitol, lactose, starches) and other excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

The pharmaceutical compositions can also be formulated in various liquid dosage forms for oral administering compounds of the invention, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention.

In accordance with one embodiment of the invention, the bioavailability enhancers are selected from organic acids. For example, the organic acid can be a monocarboxylic (such as caproic acid) or a polycarboxylic (e.g., dicarboxylic acids such as malic acid or tricarboxylic acids such as citric acid). In accordance with an embodiment of the invention the bioavailability enhancer is selected from the group consisting of ascorbic acid, citric acid, malic acid, fumaric acid, caproic acid, caprylic acid, glycocholic acid, cholic acid, and mixtures thereof. In accordance with another embodiment of the invention the bioavailability enhancer is selected from the group consisting of ascorbic acid, citric acid, malic acid, fumaric acid, and mixtures thereof. In another embodiment, the organic acid is ascorbic acid.

In addition, the bioavailability enhancer can be a pharmaceutically acceptable salt of an organic acid, e.g., sodium cholate, or other agents such as sodium lauryl sulfate and palmitoyl carnitine.

Pharmaceutically acceptable salts include those in which the main compound, the organic acid, is reacted with an appropriate base to form, e.g., sodium, potassium, calcium, magnesium, ammonium, and choline salts. Those skilled in the art will further recognize that alkali and alkaline earth metal salts are prepared by reacting the organic acids of the invention with the appropriate base via a variety of known methods.

In one embodiment, the formulations of the present invention comprise those wherein the previous and following embodiments are present, either independently or in combination.

In accordance with one embodiment of the invention, the pharmaceutical formulation contains at least one organic acid and at least one pharmaceutical agent (the ACE/NEP inhibitor(s)), wherein the pharmaceutical agent is present in the composition in an amount of from at least about 0.5 wt. %, for example, from about 0.5 wt. % to about 50 wt. %, preferably from about 1 wt. % to about 25 wt. %, and particularly about 1.0 wt. % to about 14 wt. In this embodiment, the at least one organic acid is present in the composition in an amount of from at least about 1.0 wt. %, for example, from about 1 wt. % to about 75 wt. %, especially from about 5 wt. % to about 40 wt. %.

The composition also may further excipients and additives including, for example, wetting agents, surfactants (e.g., sorbitan monooleate, sorbitan monolaurate, polysorbate, etc.), cosurfactants (e.g., cetyl alcohol, glyceryl monostearate, sodium carboxy methyl cellulose, cetyl trimethylammonium bromide, and lauryl dimethylbenzylammonium chloride), thickening agents (e.g., silicon dioxide, glyceryl behenate, etc.), binders (e.g., pregelatinized starch, alginic acid, and ethyl cellulose, etc.), disintegrants (e.g., microcrystalline cellulose, sodium starch glycolate and croscarmelose), diluents (e.g., calcium phosphate dibasic, lactose, mannitol, and powdered cellulose, etc.), adsorbents (e.g., silicon dioxide, maltodextrin, granulated calcium phosphate, etc.), antioxidants (e.g., sodium sulfite, sodium metasulfite, ethylenediamine tetraacetic acid, etc.), and processing aids such as lubricants (e.g., magnesium stearate), glidants, and antiadherants. The present invention, however, is not to be limited to the additives/excipients hereinabove described.

In accordance with the present invention, the pharmaceutical formulations can be used in the treatment or prevention of cardiovascular disorders including hypertension and heart failure. Thus, in accordance with a preferred embodiment, the present invention includes a method of treating a patient, particularly a mammal, especially a human, suffering from a cardiovascular disorder (e.g., hypertension or heart failure) comprising administering to said patient a pharmaceutically effective amount of a formulation of the present invention.

Administered dosages of the active pharmaceutical agents will depend upon a variety of factors including the particular conditions to be treated, severity of the symptoms, frequency of the dosage interval, the particular agent and its efficacy, toxicology profile, and pharmacokinetic profile, among other considerations. Typically, the ACE/NEP inhibitors are administered at dosage levels customary for such inhibitors. For example, the pharmaceutical agents can be administered, in single or multiple doses, by oral administration at a dosage level of, for example, 0.01–20 mg/kg/day, preferably 0.1–15 mg/kg/day, especially 0.35–3 mg/kg/day. Unit dosage forms can contain, for example, 0.5–200 mg of active compound(s).

The present invention will now be further described by way of the following non-limiting examples. In applying the disclosure of these examples, it should be kept clearly in mind that other and different embodiments of the methods disclosed according to the present invention will no doubt suggest themselves to those of skill in the relevant art.

In the foregoing and in the following examples, all temperatures are set forth uncorrected in degrees Celsius; and, unless otherwise indicated, all parts and percentages are by weight.

The entire disclosures of all applications, patents and publications, cited above and below, including U.S. Provisional Patent Application Serial No. 60/287,535, filed Apr. 30, 2001, are hereby incorporated by reference.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In the following examples, the materials and methods are illustrative only and not intended to be limiting.

EXAMPLES

Example 1

Preparation of Sampatrilat Formulations

In this example, powder filled capsules were prepared by screening all ingredients through a mesh 18 sieve and blending the material in a PK-Blendmaster for 10 minutes (without the inclusion of the lubricant). This was followed by a lubrication step, where the blend was passed through a mesh 20 sieve and mixed in the blender for 3 minutes with the addition of the lubricant. This material was then encapsulated into size OEL hard gelatin capsules using a PD-10 (Schaefer Technologies) semi-automatic capsule filler. The formulation can also be in the form of tablets by direct compression of the blend.

The formulations are given in Table 1 below.

TABLE 1

|  | PD0058-65 | | PD0058-54 | | PD0058-82 | | PD0058-86 | |
|---|---|---|---|---|---|---|---|---|
| Ingredients | 1 | 2 | 1 | 2 | 1 | 2 | 1 | 2 |
| Sampatrilat | 50 | 7.5 | 50 | 7.8 | 10 | 1.7 | 10 | 2.5 |
| Ascorbic acid | 250 | 37.6 | — | — | 35.7 | 6.0 | — | — |
| Calcium phosphate dibasic | 317.4 | 47.7 | 502.3 | 78.5 | 480 | 80 | 336 | 84 |
| Pregelatinized starch | 41 | 6.2 | 84.3 | 12.7 | 68.3 | 11.3 | 50 | 12.5 |
| Magnesium stearate | 6.6 | 1.0 | 6.4 | 1.0 | 6 | 1.0 | 4.0 | 1.0 |

1 = composition in mg per capsule
2 = composition in % weight
Note:
PD0058-54 and PD0058-86 contain no enhancers in the formulations. These two formulations serve as control.

A Vankel dissolution tester (Van Kel Industries, Edison, N.J.) was used for all dissolution studies. The apparatus was calibrated according to USP23. The dissolution in 0.1N hydrochloric acid (pH 1.2) was tested using the paddle method (USP Apparatus II), employing 900 ml of dissolution medium at a temperature of 37° C. and an agitation rate of 50 rpm. Samples at specific time points, i.e., 15, 30, 45, 60 min., were removed and filtered through a 10 μm filter. The filtered samples were kept in screw cap glass test tubes until analysis. An HPLC system comprised of an autosampler, a pump, and a UV detector was used for sample analysis. Samples of 50 μl in volume were injected directly into the HPLC C18 column using a mixture of pH 7.0 phosphate buffer:acetonitrile (92:8) as the mobile phase. The dissolution data are given in Table 2 below.

TABLE 2

Dissolution Data for Sampatrilat Capsule Formulations

| Time (min) | PD0058-65* | PD0058-54* |
|---|---|---|
| 15 | 86 ± 7.1 | 77 ± 9.5 |
| 30 | 92 ± 5.3 | 86 ± 9.0 |
| 45 | 94 ± 3.9 | 90 ± 9.1 |
| 60 | 96 ± 3.5 | 92 ± 8.0 |

*Note:
The data represent the mean percent dissolved ± standard deviation of six replicates.

Content uniformity tests were conducted by determining the amount of sampatrilat in each of 10 capsules (Samples A through J) using a high pressure liquid chromatography (HPLC) methodology specific for sampatrilat detection. The relative standard deviation (RSD) of the average of the 10 capsules is then taken as an indicator of content uniformity with % RSD<5.0 as passing. The content uniformity data are given in Table 3 below.

TABLE 3

Content Uniformity Data for Sampatrilat Capsule Formulations

| | PD0058-65 | |
|---|---|---|
| Sample | 1 | 2 |
| A | 48.04 | 96.1 |
| B | 45.70 | 91.4 |
| C | 47.63 | 95.3 |
| D | 46.76 | 93.5 |

TABLE 3-continued

Content Uniformity Data for Sampatrilat Capsule Formulations

| | PD0058-65 | |
|---|---|---|
| Sample | 1 | 2 |
| E | 47.74 | 95.5 |
| F | 46.69 | 93.4 |
| G | 47.05 | 94.1 |
| H | 48.29 | 96.6 |
| I | 47.32 | 94.6 |
| J | 48.61 | 97.2 |
| Mean | 47.38 | 94.8 |
| % RSD | | 1.83 |

1 = weight (mg) per capsule
2 = percent label claim per capsule

Example 2

Preparation and In Vivo Evaluation of Sampatrilat Formulations

Formulations tested were delivered in dogs as powder-filled hard gelatin capsule dosage forms with 10 mg sampatrilat. One test formulation (PD-0058-82) containing ascorbic acid as well as a reference/control formulation (PD-0058-86) were tested in vivo in dogs (n=6). The study had a 7-day washout period in between the two formulations. Plasma samples were taken from the dogs following oral administration of the capsule dosage forms. The amount of sampatrilat in dog plasma was determined using an LC/MS (liquid chromatographic/mass spectroscopic) methodology specific for sampatrilat detection. Table 4 below provides a summary of the formulations prepared. The detailed procedural description is given below.

TABLE 4

Summary of Sampatrilat Formulations

| Formulation | Composition | Average Weight of Sampatrilat (mg/capsule) | Average Total Content Weight (mg/capsule) | Lot number |
|---|---|---|---|---|
| Control Formulation | Sampatrilat/calcium phosphate dibasic/pregelatinized starch/magnesium stearate | 10 | 400 | PD0058-86 |
| Test Formulation | Sampatrilat/ascorbic acid/calcium phosphate dibasic/pregelatinized starch/magnesium stearate | 10 | 600 | PD0058-82 |

The reference/control formulation was prepared by using calcium phosphate dibasic as a diluent/filler, pregelatinized starch as a binder, and magnesium stearate as a lubricant. Pre-weighed amounts of sampatrilat (108.43 mg), dibasic calcium phosphate (3633.49 mg), and pregelatnized starch (525.52 mg) were triturated and mixed using a mortar and pestle. Magnesium stearate (45.12 mg) was then added and the blend was lubricated for ½ minute by trituration in a mortar and pestle. Appropriate amounts of this powder blend were encapsulated in size 00 Swedish orange hard gelatin capsules by hand filling. The content weight of each capsule was 397, 400, 403, 404, 411, 403, 403, and 408 mg (PD0058-86).

The test formulation was prepared similar to the reference/control formulation described above. A blend consisting of 104.05 mg sampatrilat, 369.86 mg ascorbic acid, 4812.69 mg calcium phosphate dibasic, and 648.60 pregelatinized starch was prepared by triturating the ingredients in a mortar and pestle. Magnesium stearate (63.59 mg) was then added and the blend was lubricated for ½ minute by trituration in a mortar and pestle. Appropriate amounts of this powder blend were encapsulated in size 00 Swedish orange hard gelatin capsules by hand filling. The content weight of each capsule was 599, 604, 606, 605, 609, 602, 606, and 604 mg (PD0058-82).

Figure 1:
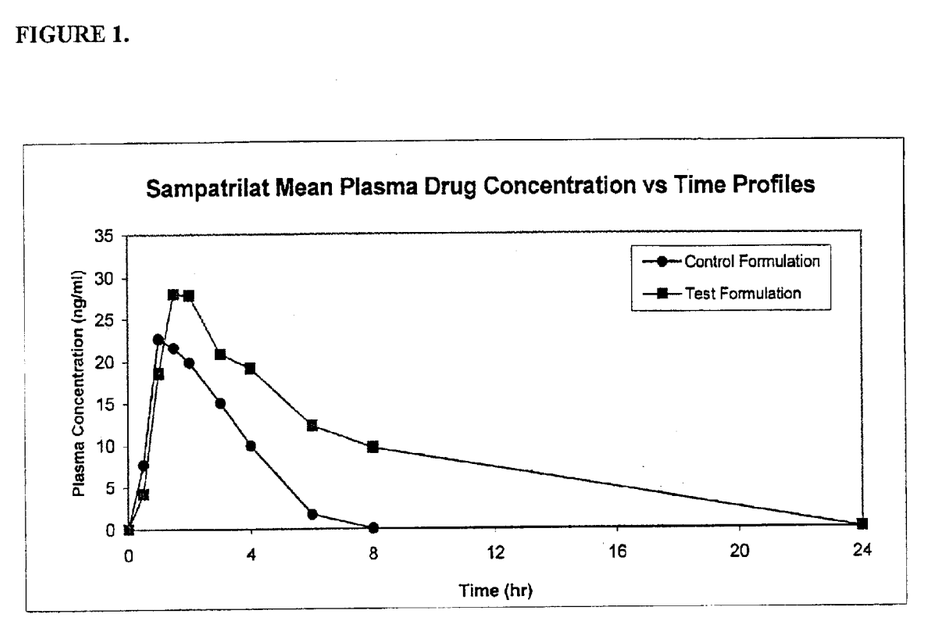
FIG. 1 illustrates the sampatrilat plasma concentration versus time profiles for formulations described in Example 2.

The average plasma concentration versus time profiles for the two formulations studied are shown in FIG. 1 and the data summarized in Table 5. The mean $C_{max}$ for the control, formulation was 25.3 ng/ml and that for the test formulation was 33.9 ng/ml. The mean $AUC_{0-24}$ for the control formulation was 76.8 ng/ml/hr versus 207.4 ng/ml/hr for the test formulation.

Using the sampatrilat intravenous injection data obtained from a canine model in a previous study, the absolute oral bioavailability of sampatrilat was calculated for the two formulations (Table 6). The test formulation containing ascorbic acid resulted in a significantly (P=0.002) greater bioavailability as compared to the control. This formulation resulted in approximately a 3-fold increase in the oral bioavailability of sampatrilat as compared to the control. Overall, ascorbic acid enhances the extent of systemic absorption of sampatrilat while maintaining a low inter-subject variability.

TABLE 5

Mean Plasma Concentration of Sampatrilat from All Formulations in Dogs (n = 6)

| | Mean Plasma Concentration (ng/mL) | |
|---|---|---|
| Time (hr) | Test Formulation | Control Formulation |
| 0 | 0.00 | 0.00 |
| 0.5 | 4.26 | 7.71 |
| 1 | 18.63 | 22.68 |
| 1.5 | 28.03 | 21.63 |
| 2 | 27.86 | 19.86 |
| 3 | 20.85 | 15.04 |
| 4 | 19.17 | 9.91 |
| 6 | 12.24 | 1.70 |
| 8 | 9.64 | 0.00 |
| 24 | 0.00 | 0.00 |
| MEAN PK PARAMETERS | | |
| $C_{max}$ (ng/ml) | 33.93 | 25.32 |
| $T_{max}$ (hr) | 2.08 | 1.42 |
| $AUC_{0-24}$ (ng/ml/hr) | 207.33 | 76.83 |

TABLE 6

Absolute Oral Bioavailability of Sampatrilat by Cross Study Comparison

| FORMULATION | Absolute Oral Bioavailability (% ± SD) |
|---|---|
| Control Formulation | 3.58 ± 0.47 |
| Test Formulation | 11.2 ± 4.26* |

*Significantly greater than the control formulation at P = 0.002

Example 3

Caco-2 Cell Line Study of Sampatrilat Formulations

A human colon carcinoma cell line, Caco-2, was grown in 150-T flasks at 37° C. in an atmosphere of 5% $CO_2$ and 95% humidity. The cells were continuously cultured in Dulbecco's modified Eagle's medium (DMEM) supplemented with 20% heat-inactivated Fetal Bovine Serum (FBS), 1% non-essential amino acids, 100 U/ml penicillin, 100 µg/ml streptomycin, and 2 mM L-glutamine. On reaching 85% confluencey, the cells were harvested by exposure to a trypsin-EDTA solution (0.25% trypsin and 0.02% EDTA in HBSS) and plated on 12 well tissue culture Transwell® plates with polycarbonate membranes. With the typical seeding density of $1 \times 10^5$ cells/cm², the cells formed monolayers between 19 and 21 days. The media was replenished three times a week and the cells were cultured for 21 days for all transport studies.

The apical buffer composed of 935 ml of Hank's Balanced Salt Solution (HBSS), 25 ml D-Glucose monohydrate (1M), 20 ml MES biological buffer (1M), 10 ml calcium chloride (125 mM), and 10 ml magnesium chloride (50 mM). The pH of the buffer was adjusted to 6.5 with potassium hydroxide.

The basolateral buffer composed of 935 ml HBSS, 25 ml D-Glucose monohydrate (1M), 20 ml HEPES biological buffer (1M), 10 ml calcium chloride (125 mM), and 10 ml magnesium chloride (50 mM). The pH of the buffer was adjusted to 7.4 with potassium hydroxide.

Sampatrilat formulations containing various excipients were then screened for the ability of the excipients to increase the permeation of the drug across the cell based model. Formulations were prepared by mixing appropriate amounts of each excipient in solutions of sampatrilat in buffer. To test sampatrilat transport across Caco-2 cell monolayers, permeation studies were conducted by placing 1.5 mL of sampatrilat formulations or controls in Hanks' Balanced Salt Solution (HBSS) were added to the upper (donor) compartment of the Transwell®, where the test samples were in contact with the apical surface of the cells. Studies were performed in six-well tissue culture plates. Transwells® were moved to a new well at 30, 60, 90, and 120 minutes giving determinations for a total of two hours. All studies were performed in triplicate. Experiments were performed in $CO_2$ incubator at 37° C. Transport was measured by taking aliquots from the lower (receiver) compartment, which were in contact with the basal surface of the cells. Aliquots were removed from each well and sampatrilat levels were determined by high performance liquid chromatography (HPLC) with UV detection.

At the end of each study, mannitol transport study was performed to confirm the integrity of the cell monolayer. Permeability studies were conducted at 10, 20, 30 and 60 minutes, and all experiments were performed in triplicate. For mannitol transport study, 3 µl of $^{14}$C-Mannitol (specific activity, 56 mCi/mmole) was added to each well and the cells were incubated at 37° C. At 10, 20, 30 and 60 minutes, 100 μl aliquot was removed from basolateral chamber and placed into 20 ml scintillation vials. Then, 10 ml of scintillation cocktail was added to each test solution and radioactivity was determined in a Beckman LS 6500 Multi-purpose Scintillation Counter.

Results are shown as enhancement ratio, which is calculated based on the amount of sampatrilat permeated in presence of enhancers divided by the control (equipotent formulation of sampatrilat in Hanks buffer without any enhancer excipients). See Tables 7–10 and FIGS. 2–5.

TABLE 7

Figure 2:
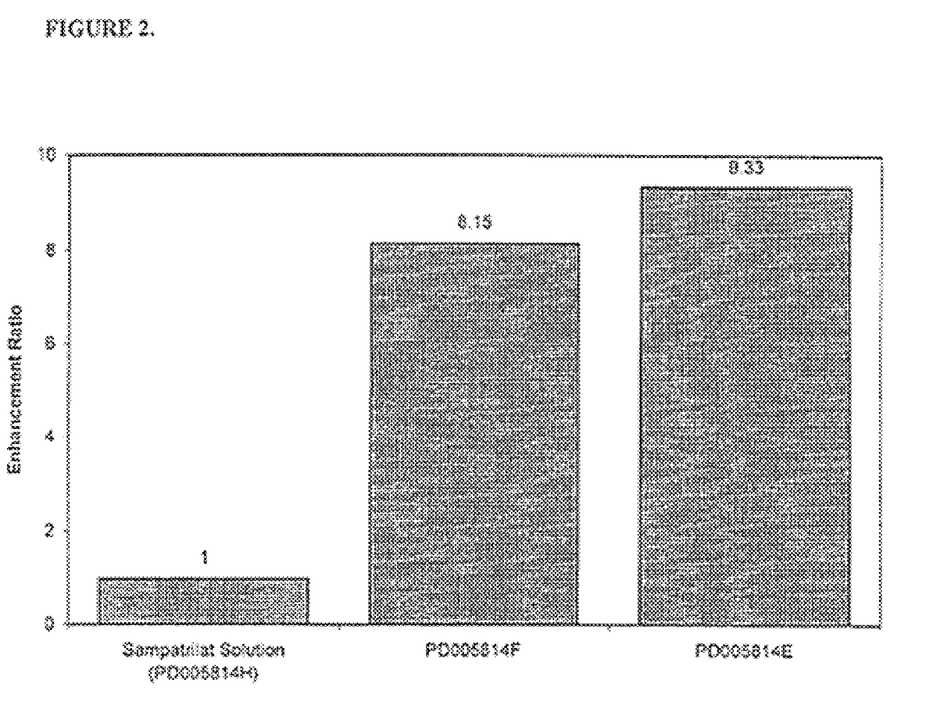
FIGS. 2–5 illustrate transport enhancement of sampatrilat across the Caco-2 model for the formulations in Example 3.

Composition of formulations illustrated in FIG. 2.

| Formulation Lot Number | Inactive Ingredient(s), % w/w | Active Ingredient (mg/g) |
|---|---|---|
| PD0058-14E | Sodium lauryl sulfate; 5%, and citric acid, 5% | Sampatrilat, 1.8 mg/g |
| PD0058-14F | Sodium lauryl sulfate, 1%, and citric acid, 5% | Sampatrilat, 1.8 mg/g |
| PD0058-14H (Control) | — | Sampatrilat, 1.8 mg/g |

TABLE 8

Figure 3:
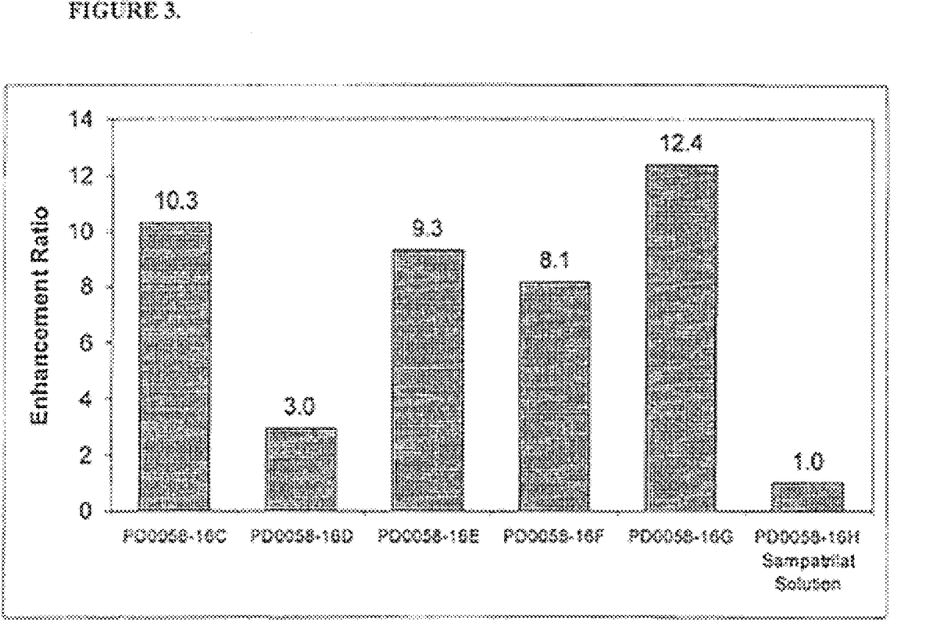

Composition of formulations illustrated in FIG. 3.

| Formulation Lot Number | Inactive Ingredient(s), % w/w | Active Ingredient (mg/g) |
|---|---|---|
| PD0058-16C | Sodium lauryl sulfate, 1% | Sampatrilat, 1.8 mg/g |
| PD0058-16D | Citric acid, 1% | Sampatrilat, 1.8 mg/g |
| PD0058-16E | Sodium lauryl sulfate, 5%, and citric acid, 5% | Sampatrilat, 1.8 mg/g |
| PD0058-16F | Sodium lauryl sulfate, 1%, and citric acid. 5% | Sampatrilat, 1.8 mg/g |
| PD0058-16G | Palmitoyl carnitine, 1.25% | Sampatrilat, 1.8 mg/g |
| PD0058-16H (Control) | — | Sampatrilat, 1.8 mg/g |

TABLE 9

Figure 4:
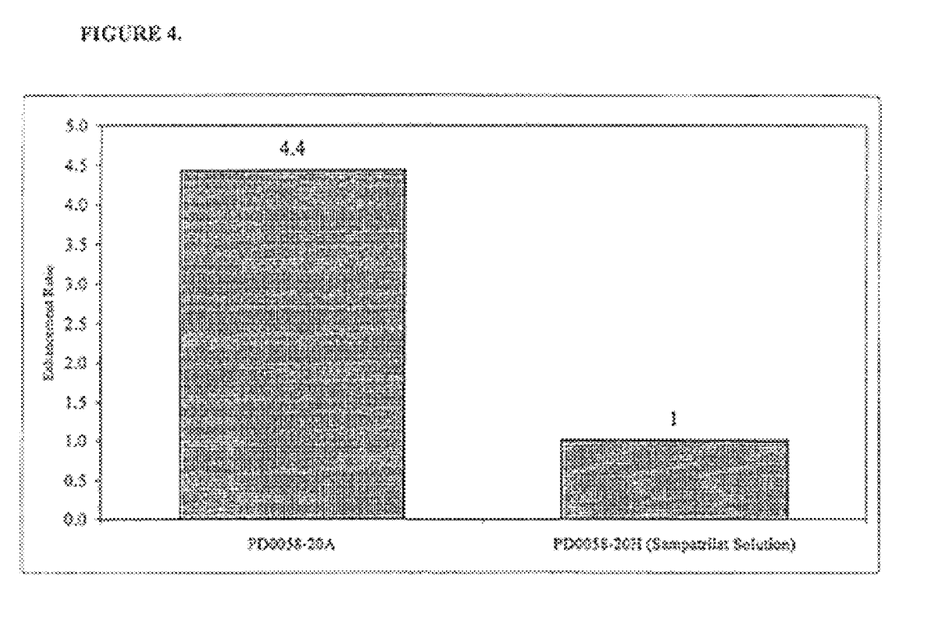

Composition of formulations illustrated in FIG. 4.

| Formulation Lot Number | Inactive Ingredient(s), % w/w | Active Ingredient (mg/g) |
|---|---|---|
| PD0058-20A | Fumaric acid, 10% | Sampatrilat, 1.8 mg/g |
| PD0058-20H (Control) | — | Sampatrilat, 1.8 mg/g |

TABLE 10

Figure 5:
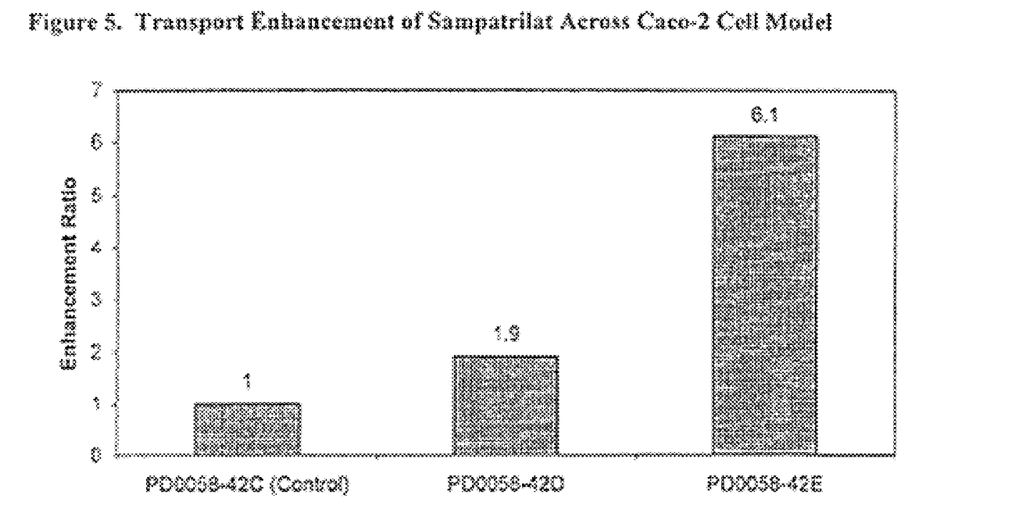

Composition of formulations illustrated in FIG. 5.

| Formulation Lot Number | Inactive Ingredient(s), % w/w | Active Ingredient (mg/g) |
|---|---|---|
| PD0058-42C (Control) | — | Sampatrilat, 1.8 mg/g |
| PD0058-42D | Ascorbic acid, 1.0% | Sampatrilat, 1.8 mg/g |
| PD0058-42E | Ascorbic acid, 0.1% | Sampatrilat, 1.8 mg/g |

Example 4

Further Caco-2 Cell Line Study of Sampatrilat Formulations

A total of 140 single excipients or combinations there-of were screened similar to that explained in example 3. Excipients providing for significant enhancement are listed in Table 11.

TABLE 11

List of excipients providing for significant permeation enhancement

Caproic acid
Caprylic acid
Citric acid
Malic acid
Glycocholic acid
Cholic acid
Sodium cholate
Sodium lauryl sulfate
Palmitoyl carnitine
Ascorbic acid Example 5

Further In Vivo Evaluation of Sampatrilat Formulations

In vitro/in vivo correlation (IVIVC) was established by testing the excipients showing significant permeation enhancement in vitro in a canine model for in vivo assessment. Formulations tested were delivered orally as powder filled hard gelatin capsule dosage forms with 10 mg sampatrilat. Three formulations containing the enhancers as well as a control formulation were tested. The first formulation consisted of calcium phosphate dibasic as filler/diluent, pregelatinized starch as disintegrant, magnesium stearate as lubricant, and ascorbic acid as absorption enhancer (PD0058-77). The second formulation was similar in composition to the first formulation except for the ratio of drug to enhancer, where the amount of ascorbic acid was reduced by 75% (PD0058-82). This was intended to determine the effect of altered drug:enhancer ratio on bioavailability. The third formulation consisted of the same filler/diluent, disintegrant, and lubricant as that in the other formulations, however the absorption enhancer used was palmitoyl carnitine (PD0058-83). The control formulation (PD0058-86) contained all the same ingredients as for the test formulations except for the fact that it did not contain any potential absorption enhancers.

Table 12 provides the composition of all formulations tested in this study. For each formulation, a total of 8 capsules was formulated and submitted to TherImmune Research Corp., Gaithersburg, Md. where the study was carried out using 6 dogs for each phase of the experiment.

TABLE 12

Summary of Sampatrilat Formulations

| Ingredients | PD0058-77 Formulation #1 | | PD0058-82 Formulation #2 | | PD0058-83 Formulation #3 | | PD0058-86 Control | |
|---|---|---|---|---|---|---|---|---|
| | 1 | 2 | 1 | 2 | 1 | 2 | 1 | 2 |
| Sampatrilat | 10 | 1.67 | 10 | 1.67 | 10 | 1.67 | 10 | 2.50 |
| Ascorbic acid | 142 | 23.67 | 35.7 | 5.95 | — | — | — | — |
| Palmitoyl | — | — | — | — | 100 | 16.67 | — | — |

TABLE 12-continued

Summary of Sampatrilat Formulations

|  | PD0058-77 Formulation #1 | | PD0058-82 Formulation #2 | | PD0058-83 Formulation #3 | | PD0058-86 Control | |
|---|---|---|---|---|---|---|---|---|
| Ingredients | 1 | 2 | 1 | 2 | 1 | 2 | 1 | 2 |
| carnitine HCl | | | | | | | | |
| Pregelatinized starch | 45 | 7.50 | 68.3 | 11.38 | 50 | 8.33 | 50 | 12.50 |
| Calcium phosphate dibasic | 397 | 66.16 | 480 | 80.00 | 434 | 72.33 | 336 | 84.00 |
| Magnesium stearate | 6 | 1.00 | 6 | 1.00 | 6 | 1.00 | 4 | 1.00 |

1 = composition in mg per capsule
2 = composition in % weight

The control formulation was prepared by using a blend consisting of 108.43 mg sampatrilat, 3633.49 mg calcium phosphate dibasic, 525.52 mg pregelatinized starch, and 45.12 mg magnesium stearate. The material (without magnesium stearate) was triturated and mixed using a mortar and pestle. Magnesium stearate was then added and the blend was lubricated by trituration in the mortar and pestle. An appropriate amount of this powder blend was encapsulated in size 00 Swedish orange hard gelatin capsules by hand filling. The fill weight of each capsule was 397, 400, 403, 404, 411, 403, 402, and 408 mg (PD0058-86).

Formulation #1 was prepared similar to the control formulation using a blend consisting of 107.40 mg sampatrilat, 1495.00 mg ascorbic acid, 4000.00 mg calcium phosphate dibasic, 446.60 mg pregelatinized starch, and 56.40 mg magnesium stearate. The fill weight of each capsule was 599, 600, 598, 601, 599, 598, 603, and 598 mg (PD0058-77).

Formulation #2 was also prepared similar to that outlined for the control formulation. The blend consisted of 104.05 mg sampatrilat, 369.86 ascorbic acid, 4812.69 mg calcium phosphate dibasic, 648.60 mg pregelatinized starch, and 63.59 mg magnesium stearate. The fill weight of each capsule was 599, 604, 606, 605, 609, 602, 606, and 604 mg (PD0058-82).

As with Formulations #1 and #2, Formulation #3 was also prepared as outlined for the control formulation. The blend consisted of 109.61 mg sampatrilat, 999.47 mg palmitoyl carnitine (DL), 4425.33 mg calcium phosphate dibasic, 520.46 mg pregelatinized starch, and 63.18 mg magnesium stearate. The fill weight of each capsule was 601, 605, 614, 595, 613, 599, 614, and 597 mg (PD0058-83).

Figure 6:
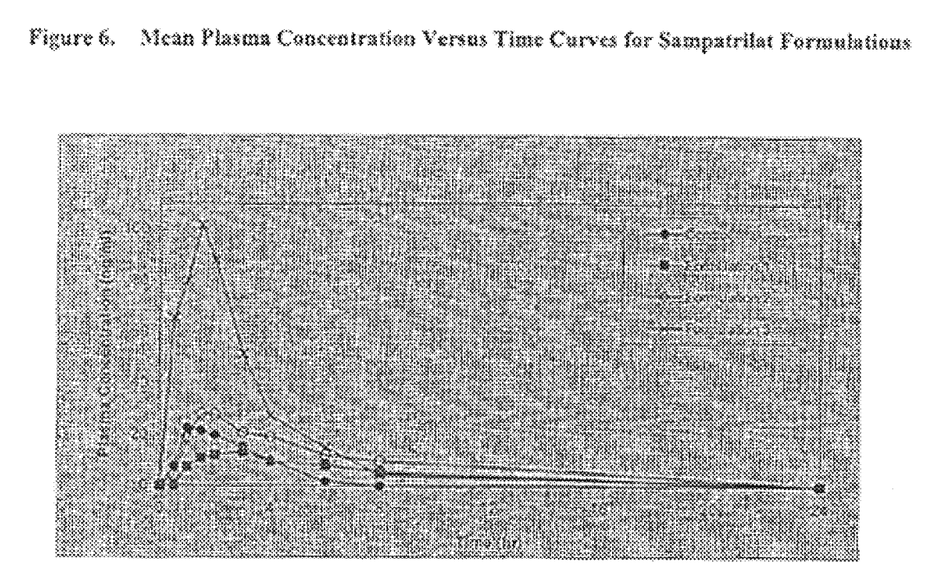
FIG. 6 illustrates the sampatrilat plasma concentration versus time profiles for formulations described in Example 6.

The average plasma concentration versus time profiles for all formulations studied are shown in FIG. 6. Table 13 lists the mean PK parameters. The mean $C_{max}$ for control, formulation #1, formulation #2, and formulation #3 were 25, 16, 34 and 128 ng/mL, respectively. The mean $AUC_{0-24}$ for control, formulation #1, formulation #2, and formulation #3 were 77, 108, 207 and 351, respectively. All three formulations were effective in increasing the $AUC_{0-24}$ as compared to the control.

TABLE 13

Mean Pharmacokinetic (PK) Parameters

| PK Parameter | FORMULATION #1 | Formulation #2 | Formulation #3 | Control |
|---|---|---|---|---|
| $T_{max}$ (hr) | 2.20 | 2.08 | 0.92 | 1.42 |
| $C_{max}$ (ng/ml) | 16.15 | 33.93 | 127.74 | 25.32 |
| $AUC_{0-24}$ (ng.hr/ml) | 108 | 207 | 351 | 77 |
| Ratio $C_{max}$ | 0.64 | 1.34 | 5.05 | 1.00 |
| Ratio $AUC_{0-24}$ | 1.40 | 2.70 | 4.58 | 1.00 |

These results further confirm the existence of an in vitro-in vivo correlation between the Caco-2 cell based screening model and systemic drug absorption of sampatrilat in dogs. All three formulations tested in vivo resulted in enhanced sampatrilat absorption as compared to the control formulation, thus in vitro/in vivo correlation (IVIVC) was achieved.

It is to be understood that, within the scope of the present invention, that formulation variations (such as multiparticulate systems, multilayered tablets, modified release systems, and osmotically controlled systems) as well as various administration routes (such as buccal, nasal, rectal, etc.) may be employed.

It is to be understood, however, that the scope of the present invention is not to be limited to the specific embodiments described above. The invention may be practiced other than as particularly described and still be within the scope of the accompanying claims.

What is claimed is:

1. A pharmaceutical composition comprising at least one dual inhibitor of angiotensin converting enzyme and neutral endopeptidase, and at least one bioavailability enhancer selected from ascorbic acid, citric acid, malic acid, fumaric acid, and pharmaceutically acceptable salts of said acids.

2. The pharmaceutical composition according to claim 1, wherein said at least one dual inhibitor is chosen from among sampatrilat, fasidotril, and omapatrilat.

3. The pharmaceutical composition according to claim 1, which comprises sampatrilat as the only dual inhibitor.

4. The pharmaceutical composition according to claim 1, wherein the bioavailability enhancer is ascorbic acid.

5. The pharmaceutical composition according to claim 1, which contains at least 0.5 wt. % of at least one dual inhibitor, and at least 1 wt. % of at least one enhancer.

6. The pharmaceutical composition according to claim 1, wherein said dual inhibitor(s) is present in an amount of from about 0.5 wt. % to about 50 wt. %.

7. The pharmaceutical composition according to claim 6, wherein said dual inhibitor is present in an amount of from about 1 wt. % to about 26 wt. %.

8. The pharmaceutical composition according to claim 1, wherein said bioavailability enhancer(s) is present in an amount of from about 1 wt. % to about 75 wt %.

9. The pharmaceutical composition according to claim 8, wherein said bioavailability enhancer(s) in an amount of from about 5 wt. % to about 40 wt. %.

10. The pharmaceutical composition according to claim 3, wherein said dual inhibitor is present in an amount of from 0.5 wt. % to about 50 wt. %.

11. The pharmaceutical composition according to claim 10, wherein said dual inhibitor is present in an amount of from about 1 wt. % to about 25 wt. %.

12. The pharmaceutical composition according to claim 4, wherein the ascorbic acid is present in an amount of from about 1 wt. % to about 75 wt. %.

13. The pharmaceutical composition according to claim 12, wherein the ascorbic acid is present in an amount of from about 5 wt. % to about 40 wt. %.

14. The pharmaceutical composition according to claim 3, wherein the bioavailability enhancer is ascorbic acid.

15. A method for treating a cardiovascular disorder in a patient, comprising administering to said patient a pharmaceutically effective amount of a composition according to claim 1.

16. The method of claim 15, wherein said composition is comprised of sampatrilat and ascorbic acid.

17. A process for preparing a pharmaceutical composition, comprising combining at least one agent, in powder form, selected from the group consisting of dual inhibitors of angiotensin convening enzyme and neutral endopeptidase, with at least one bioavailability enhancer selected from ascorbic acid, citric acid, malic acid, fumaric acid, and pharmaceutically acceptable salts of said acids, also in powder form to obtain a powdered mixture and either (a) encapsulating said powdered mixture in a capsule or (b) forming said powdered mixture into a tablet.

18. The process of claim 17, wherein the composition is comprised of sampatrilat and ascorbic acid.

* * * * *